United States Patent [19]

Fuentes

[11] Patent Number: 4,845,261

[45] Date of Patent: Jul. 4, 1989

[54] PROCESS FOR BIS(SUBSTITUTED PHENYL) PHOSPHOROHALIDATES

[75] Inventor: Lelia M. Fuentes, Westfield, N.J.

[73] Assignee: Merck & Co., Inc., Rahway, N.J.

[21] Appl. No.: 48,342

[22] Filed: May 11, 1987

[51] Int. Cl.$^4$ ............................................. C07F 9/14
[52] U.S. Cl. .................................................... 558/101
[58] Field of Search ......................................... 558/101

[56] References Cited

U.S. PATENT DOCUMENTS

| | | | |
|---|---|---|---|
| 3,689,602 | 9/1972 | Ismail | 260/936 |
| 3,772,414 | 11/1973 | Baker | 260/973 |
| 3,965,220 | 6/1976 | Schumacher | 260/975 |
| 4,059,655 | 11/1977 | Carno | 558/101 |

FOREIGN PATENT DOCUMENTS 1193031  5/1965  Fed. Rep. of Germany ...... 558/101

OTHER PUBLICATIONS

G. Hofle, W. Steglich, H. Vorbruggen, "4-Dialkylaminopyridines as Highly Active Acylation Catalysts," Angew. Chem. Int. Ed. Engl., 17, 569–583 (1978).

*Primary Examiner*—Anton H. Sutto
*Attorney, Agent, or Firm*—Raymond M. Speer; Hesna J. Pfeiffer

[57] ABSTRACT

This invention relates to a novel process for preparing bis(substituted phenyl) phosphorohalidates.

11 Claims, No Drawings

PROCESS FOR BIS(SUBSTITUTED PHENYL) PHOSPHOROHALIDATES

BACKGROUND OF THE INVENTION (a) Field of the Invention

This invention relates to a novel and advantageous process for preparing bis(substituted phenyl)phosphorohalidates. In particular, this invention relates to a process for preparing bis(2,4-dichlorophenyl)phosphorochloridate, which is useful as a phosphorylating reagent. More specifically, the process is useful for preparing bis(2,4-dichlorophenyl)phosphorochloridate compositions that are useful in the synthesis of enol phosphate intermediates that can be used in the manufacture of certain carbapenem antibiotics.

(b) Prior Art

Various processes for preparing bis(substituted phenyl)phosphorohalidates have been disclosed. For example, U.S. Pat. No. 3,965,220 discloses a process in which aromatic alcohols and phosphorus halides are allowed to react in the presence of amine catalysts to form various esters of phosphorus acids, including phosphorochloridate esters. Unlike the process of the present invention, however, the process of the U.S. Pat. No. 3,965,220 involves a two-stage procedure in which monoesters are formed initially at 85°–135° (preferably 105°) and diesters are then formed, after addition of more phenol, at 130°–165° (preferably 150°). Although the claims of the U.S. Pat. No. 3,965,220 give a temperature range of 85°–165° for preparing "a mono or diester," the specification discloses methods that describe only the range of 85°–135° for monoesters and 130°–165° for diesters. The process of the present invention, by contrast, provides diesters in a one-stage procedure performed within a single temperature range that can be lower than the 130°–165° range required by the U.S. Pat. No. 3,965,220. Moreover, dialkylaminopyridines are not among the amine catalysts disclosed in the U.S. Pat. No. 3,965,220. In the process of the present invention dialkylaminopyridines have been found to possess surprisingly advantageous chemical and physical properties not suggested by the U.S. Pat. No. 3,965,220. The preferred method of isolation used in the present invention provides another distinction from the U.S. Pat. No. 3,965,220: The isolation by crystallization used in the present invention provides a convenient and economically advantageous method for isolating bis(substituted phenyl)phosphorochloridates, in contrast to the distillation method disclosed in the U.S. Pat. No. 3,965,220.

U.S. Pat. No. 3,772,414 discloses a process similar to that of the U.S. Pat. No. 3,965,220 except that various ureas instead of amines are used as catalysts. In addition to the differences discussed above for the U.S. Pat. No. 3,965,220, the present invention differs from the U.S. Pat. No. 3,772,414 in that ureas are not used as catalysts.

U.S. Pat. No. 3,689,602 discloses a process in which 2,4-dichlorophenol and phosphorus oxychloride are allowed to react in the presence of heteroaromatic amines, such as pyridine, to form tris(2,4-dichlorophenyl)phosphate. The U.S. Pat. No. 3,689,602 does not suggest the use of dialkylaminopyridines. Moreover, the U.S. Pat. No. 3,689,602 does not suggest the preparation of phosphorochloridate diesters but is instead specifically limited to the preparation of phosphotriesters.

SUMMARY OF THE INVENTION

Applicants have discovered an advantageous process for preparing bis(substituted phenyl)phosphorohalidates of Formula I

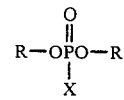

wherein

R is phenyl or phenyl substituted with 1 to 3 substituents selected from the groups consisting of:
 (i) halogen;
 (ii) $C_1$–$C_6$ alkyl;
 (iii) $C_1$–$C_6$ alkoxy;
 (iv) $C_1$–$C_4$ fluorinated alkyl; or
 (v) $NO_2$; and X is chlorine or bromine.

Examples of halogen are fluorine, chlorine, bromine, and iodine.

The term "$C_1$–$C_6$ alkyl" refers to straight or branched chain aliphatic hydrocarbon groups having from 1 to 6 carbon atoms, also referred to as lower alkyl. Examples of $C_1$–$C_6$ alkyl are methyl, ethyl, propyl, butyl, pentyl, hexyl, and the isomeric forms thereof.

The term "$C_1$–$C_6$ alkoxy" refers to straight or branched chain alkyl oxy groups having from 1 to 6 carbon atoms. Examples of $C_1$–$C_6$ alkoxy are methoxy, ethoxy, propoxy, butoxy, pentoxy, hexoxy, and the isomeric forms thereof.

The term "$C_1$–$C_4$ fluorinated alkyl" refers to straight or branched chain alkyl groups in which one or more hydrogen atoms are replaced with fluorine atoms. Examples of $C_1$–$C_4$ fluorinated alkyl are fluoromethyl, difluoromethyl, trifluoromethyl, 1- or 2-fluoroethyl, 1,1-difluoroethyl, 2,2,2-trifluoroethyl, perfluoroethyl; other similarly monofluorinated, polyfluorinated, and perfluorinated ethyl, propyl, and butyl groups; and the isomeric forms thereof.

More specifically, this invention relates to a process for preparing phosphorohalidates of Formula I by which a phosphorus oxyhalide is allowed to react with a substituted phenol in the presence of a dialkylaminopyridine or hydrohalide salt thereof. This invention also relates to the above process by which the phosphorohalidates of Formula I may be isolated by crystallization using a substantially inert crystallization solvent. This invention further relates to recovery and recycling of dialkylaminopyridine hydrohalide salts recoverable in the crystallization aspect of this invention.

DESCRIPTION OF THE INVENTION

The process of this invention may be effectuated by the general procedures illustrated in the following Scheme A. Unless otherwise specified, the various substituents are defined as for Formula I, above.

SCHEME A

R—OH    II

↓ POX₃

-continued
SCHEME A

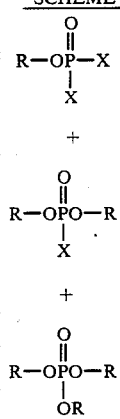

Reaction of a substituted phenol of Formula II with a phosphorus oxyhalide of the formula $POX_3$ (where X is chlorine or bromine) can, depending upon the particular reaction conditions employed, yield compounds of Formula I, III, and IV, either as the substantially pure individual components or as various mixtures thereof. The present invention is a process for preparing bis(substituted phenyl)phosphorohalidates of Formula I containing varying quantities of tris(substituted phenyl)phosphates of Formula IV but being substantially free of (substituted phenyl)phosphorodihalidates of Formula III. Under the reaction conditions of this invention, a phosphorus oxyhalide is allowed to react with an approximately one-fold to two-fold molar quantity of a phenol of Formula II in the presence of a suitable dialkylaminopyridine or hydrohalide salt thereof.

The preferred molar ratio of phenol to phosphorus oxyhalide is from about 1.3:1 to about 1.9:1. The reaction may optionally be performed in a suitable organic solvent but is usually performed without adding a separate solvent. Where a solvent is used, a suitable organic solvent includes organic liquids in which reactants may be dissolved or suspended but which are otherwise chemically inert, and in which reactants may be heated to at least about 100° C. but not significantly higher than the boiling points of the reactants. For example, the boiling point of phosphorus oxychloride is about 106° C. and that of phosphorus oxybromide is about 193° C. Examples of suitable organic solvents include higher boiling alkanes and cycloalkanes, such as heptane, octane, cycloheptane, and the like; ethers and cyclic ethers, such as dibutyl ether and the like; aromatic hydrocarbons, such as toluene, xylene, and the like; halocarbons, such as tetrachloroethane, tetrachloroethylene, and the like; and other solvents known in the art. The reaction is preferably performed without adding a separate solvent. Whether performed with or without a separate solvent, the reaction must be performed at temperatures and pressures such that the ratio of reactants is not significantly affected by evaporative losses. For example, at atmospheric pressure and temperatures above about 120°-130° C., loss of phosphorus oxychloride can affect the relative proportions of compounds of Formulas I, III, and IV that are produced in the reaction. In particular, loss of phosphorus oxychloride can be expected to increase the amounts of compounds IV relative to the desired compounds I.

The phosphorylation reactions involved in the process of this invention are promoted by suitable dialkylaminopyridines. For the purposes of this invention, the term "dialkylaminopyridine" includes pyridine substituted at the 2- or 4-position (preferably the 4-position) with an N,N-di($C_1$–$C_6$ alkyl)amino group; an N,N-di($C_4$–$C_7$ cycloalkyl)amino group; an N-($C_1$–$C_6$ alkyl)-N-($C_4$–$C_7$ cycloalkyl)amino group; or a 1-azacycloalkyl group having from 4 to 7 ring nucleus atoms, the 1-azacycloalkyl group being optionally substituted at one or more ring carbon atoms by $C_1$–$C_6$ alkyl. Examples of N,N-di($C_1$–$C_6$ alkyl)amino include N,N-dimethylamino, N,N-diethylamino, N-ethyl-N-methylamino, and the like. Examples of N,N-di($C_4$–$C_7$ cycloalkyl)amino include N,N-dicyclopentylamino, N,N-dicyclohexylamino, N-cyclohexyl-N-cyclopentylamino, N,N-dicylohexylamino, N-cyclohexyl-N-cyclopentylamino, and the like. Examples of N-($C_1$–$C_6$ alkyl)-N-($C_4$–$C_7$ cycloalkyl)amino include N-cyclopentyl-N-methylamino, N-cyclohexyl-N-methylamino, N-cyclohexyl-N-ethylamino, and the like. Examples of 1-azacycloalkyl include 1-pyrrolidinyl, 1-piperidinyl, and the like, and optionally alkyl-substituted derivatives thereof, such as 4-methyl-1-piperidinyl and the like. A preferred dialkylaminopyridine is 4-dimethylaminopyridine.

A dialkylaminopyridine need not be present in a stoichiometric amount but instead may be present in a catalytic amount, typically in the range of 1 to 10 molar percent relative to the phosphorus oxyhalide. Moreover, hydrohalide salts of dialkylaminopyridines are essentially equally effective at promoting the reaction. Preferred dialkylaminopyridine salts include 4-dimethylaminopyridine hydrochloride and hydrobromide. Where a salt of a dialkylaminopyridine or only a catalytic amount of a dialkylaminopyridine is used, the hydrogen halide produced in the reaction is typically allowed to escape the reaction mixture as a gas that, if desired, can be trapped, for example, in a scrubber.

Various chemical and physical properties make 4-dimethylaminopyridine a particularly advantageous dialkylaminopyridine for the process of this invention. Chemical properties make 4-dimethylaminopyridine an exceptional catalyst for acylations when compared to pyridine or other amines. For a review of such properties, see Hofle, Steglich, and Vorbruggen, *Angew. Chem. Int. Ed. Engl.*, 17, 569–583 (1978). One might except similarly exceptional behavior for phosphorylations. See, for example, Hofle, Steglich, and Vorbruggen at p. 575. Certain physical properties of 4-dimethylaminopyridine and its hydrochloride salt also provide distinct advantages. Both the free amine and its hydrochloride salt are crystalline solids at ordinary temperatures. Moreover, the free amine is essentially non-hygroscopic and the hydrochloride salt seems less hygroscopic than is usual for amine hydrochlorides. Thus, 4-dimethylaminopyridine and its hydrochloride salt are easily manipulated, an advantage when working with the water-sensitive reactants used in the process of this invention. Where the process of this invention is performed without adding a separate solvent, 4-dimethylaminopyridine can be removed as the hydrohalide salt by adding a suitable crystallization solvent as described below. The salt can be essentially completely recovered and then recycled, a feature of the process having distinct advantages in a commercial application. For example, recovery and recycling of the salt permits optimization of the reaction with less concern for the economics of lost amine catalyst.

The desired bis(substituted phenyl)phosphorohalidates may be isolated by any of several methods known in the art. For example, fractional distillation has been used to isolate such compounds. See, e.g., U.S. Pat. No. 3,965,220. A preferred method of isolation is crystallization, a method having distinct practical and economic advantages over energy-consuming distillation methods. Crystallizations used in this invention employ a substantially inert crystallization solvent. The term "substantially inert crystallization solvent" refers to a liquid with which the desired bis(substituted phenyl)-phosphorohalidate is substantially chemically unreactive and in which the desired bis(substituted phenyl)-phosphorohalidate is essentially completely soluble when warmed up to and including the solvent's boiling point but is substantially insoluble when cooled to convenient temperature ranging from about 0° C. down to about −40° C. Where the phosphorylation reaction is performed with a separate solvent, that same solvent may be used for the crystallization if the above solubility requirements are satisfied; otherwise, the reaction solvent must first be substantially removed. Where the phosphorylation reaction is performed without a separate solvent, the crystallization solvent may be added directly to the reaction mixture, which should preferably first be cooled to a temperature below the boiling point of the crystallization solvent. One skilled in the art could readily determine the quantities of crystallization solvent required and the optimum temperatures to be used. Examples of substantially inert crystallization solvents include alkanes and cycloalkanes, such as pentane, hexane, heptane, octane, nonane, cyclopentane, cyclohexane, and the like; ethers and cyclic ethers, such as diethyl ether, dipropyl ether, tetrahydrofuran, tetrahydropyran, and the like; aromatic hydrocarbons, such as benzene, toluene, and the like; halocarbons, such as chloroform, dichloromethane, and the like; and other solvents known in the art. Preferred crystallization solvents include those solvents in which dialkylaminopyridine hydrohalide salts are essentially completely insoluble at temperatures well above the temperature at which crystallization of the desired bis(substituted phenyl)phosphorohalidate is effectuated. Preferred crystallization solvents include alkanes of from about 5 carbon atoms to about 9 carbon atoms. In the preferred embodiment of this invention wherein the desired product is bis(2,4-dichlorophenyl)phosphorochloridate and the preferred dialkylaminopyridine is 4-dimethyl-aminopyridine, the preferred crystallization solvent is hexane. It is understood that the term "hexane" refers to n-hexane, its isomers, and commercially available mixtures thereof. As illustrated in the Examples, the use of hexane as crystallization solvent permits removal, preferably by filtration, of various insoluble materials, including 4-dimethylaminopyridine hydrochloride (which can easily be recycled), and permits convenient isolation, preferably by filtration, of the desired bis(2,4-dichlorophenyl)phosphorochloridates at temperatures between about −10° C. and −40° C.

The preferred embodiment of this invention involves a process for preparing bis(2,4-dichlorophenyl)phosphorochloridate having the Formula V

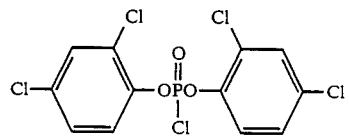

comprising (a) reacting phosphorus oxychloride with an approximately 1.2-fold to 2.0-fold molar quantity of 2,4-dichlorophenol in the presence of 4-dimethylaminopyridine or 4-dimethylaminopyridine hydrochloride at a temperature of about 120°;

(b) adding hexane at a temperature below the boiling pont of hexane;

(c) removing insoluble material from a resultant solution of the bis(2,4-dichlorophenyl)phosphorochloridate in hexane;

(d) cooling the solution to a temperature of from about 0° to about −40°, preferably from about −15° to about −30°; and (e) collecting the bis(2,4-dichlorophenyl)phosphorochloridate by filtration.

The bis(substituted phenyl)phosphorohalidate compositions of this invention may be used as phosphorylating reagents. More specifically, the phosphorohalidate is useful in the preparation of certain enol phosphate intermediates that can be used in the manufacture of certain carbapenem antibiotics. Where the phosphorohalidate is bis(2,4-dichlorophenyl)phosphorochloridate, formation of such enol phosphate intermediates has been found to be unaffected by the presence of up to at least 20% tris(2,4-dichlorophenyl)phosphate contamination, as illustrated in Examples 3 and 4.

The following examples further illustrate details for the process of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

Phosphorochloridate and related product analyses were performed using gas-liquid partition chromatography (GLPC) on a 15 m×0.25 mm flexible fused silica capillary column wall coated with a methyl silicone. The gas chromatograph was equipped with a split mode capillary injection system and a flame ionization detector. Injector and detector temperatures were 250° and 300°, respectively. During analyses the oven temperature was held at 125° for two minutes, then raised at 20° per minute until reaching 250°. Retention times were determined using known samples of 2,4-dichlorophenyl phosphorodichloridate, bis(2,4-dichlorophenyl)phosphorochloridate, and tris(2,4-dichlorophenyl)phosphate. Eicosane was used as internal standard.

Thienamycin and related carbapenem product analyses were performed using high performance liquid chromatography (HPLC) procedures commonly used by those skilled in the art.

DESCRIPTION OF THE PREFERRED EMBODIMENTS

EXAMPLE 1

Bis(2,4-dichlorophenyl)phosphorochloridate, Method A

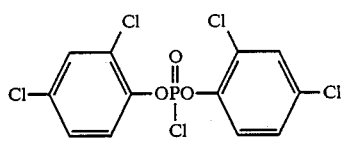

To a melt of 2,4-dichlorophenol (400.0 g, 2.454 mole) at ca. 50° was added 4-dimethylaminopyridine (6.93 g, 56 mole), followed by phosphorus oxychloride (289.5 g, 1.887 mole). The mixture was heated under nitrogen to ca. 120°, at which temperature the mixture began to reflux and to generate hydrogen chloride (which was passed through a sodium hydroxide scrubber). After about twelve hours at 120°–125°, GLPC indicated less than 1% (by weight) of unreacted 2,4-dichlorophenol and a mixture of 2,4-dichlorophenyl phosphorodichloridate, the desired bis(2,4-dichlorophenyl)phosphorochloridate, and tris(2,4-dichlorophenyl)phosphate. After the reaction mixture was cooled to ca. 40°, hexane (145 ml) was added and the mixture was cooled to ca. 20°. A precipitate containing 4-dimethylaminopyridine hydrochloride was removed by filtration. The filtrate was diluted with additional hexane (145 ml) and cooled to ca. −30°. After about eight hours the resultant precipitate was collected by filtration and washed with hexane (four 200-ml portions) at ca. −20°, all with careful exclusion of moisture. Drying for two hours at room temperature under a flow of nitrogen yielded 129.87 g (26% yield) of the desired bis(2,4-dichlorophenyl)phosphorochloridate as a white solid. Analysis by GLPC indicated 99% purity (by weight), with contamination by 0.3% (by weight) 2,4-dichlorophenyl phosphorodichloridate and 0.2% (by weight) tris(2,4-dichlorophenyl)phosphate.

EXAMPLE 2

Bis(2,4-dichlorophenyl)phosphorochloridate, Method B

The title compound was prepared by the general method of Example 1 with the following modifications. (1) The molar ratio of 2,4-dichlorophenol to phosphorus oxychloride was increased from 1.33 to 1.85 by using 189.99 g (1.165 mole) of 2,4-dichlorophenol and 96.60 g (0.63 mole) of phosphorus oxychloride. (2) The reaction time at 120° was increased to about 24 hours. (3) The product was crystallized using a larger quantity of hexane (570 ml, or 3 ml per gram of starting 2,4-dichlorophenol) at −15°. Analysis by GLPC indicated 82% purity (by weight) of bis(2,4-dichlorophenyl)phosphorochloridate, with contamination by a trace of 2,4-dichlorophenyl phosphorodichloridate and 18% (by weight) of tris(2,4-dichlorophenyl)phosphate. The yield of the bis(2,4-dichlorophenyl)phosphorochloridate when corrected for purity was 125 g (53%). Subsequent reactions were unaffected by the presence of the tris(2,4-dichlorophenyl)phosphate, as illustrated by Examples 3 and 4.

EXAMPLE 3

N-Formamidoylthienamycin, Method A

Step A

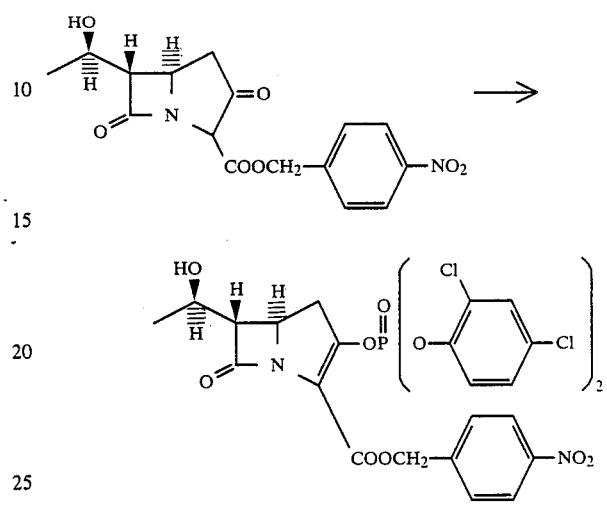

To a cooled (−50°) solution of p-nitrobenzyl (3R,5R,6S)-2-oxo-6-[(1R)-1-hydroxyethyl]carbapenem-3-carboxylate (1.964 g, 5.64 mmoles) in N-ethyl-pyrrolidinone (24.11 g) was added diisopropylethylamine (1.75 g, 13.5 mmoles) followed by bis(2,4-dichlorophenyl)phosphorochloridate (2.45 g, 6.03 mmole; see Example 1). The mixture was stirred for two hours and used in the next step without isolation of the enol phosphate intermediate.

Step B

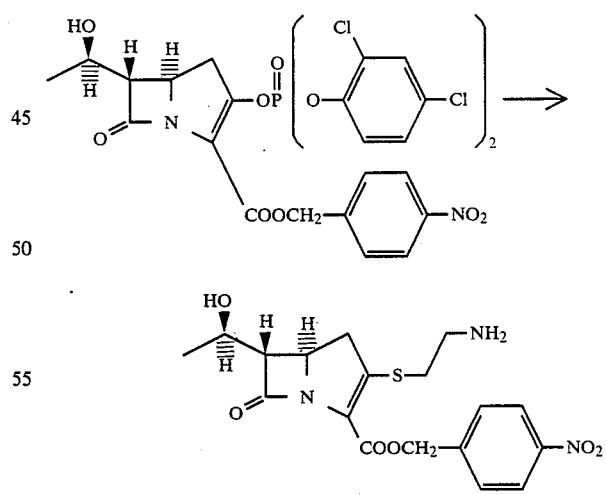

The reaction mixture from Step A was cooled to −62°. A solution of cysteamine hydrochloride (0.70 g, 6.16 mmoles) in N-ethylpyrrolidinone (2 ml) was added over a five-minute period, during which time the temperature was maintained below −60°. The reaction was stirred at −60° for 1.5 hours and used in the next step without isolation of the aminoethylthio intermediate.

Step C

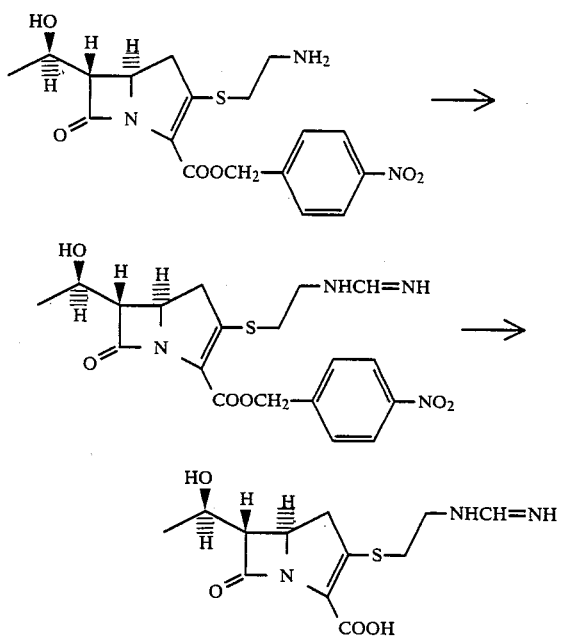

Amidine formation and hydrogenolysis of the ester group were performed using the general method described in U.S. Pat. No. 4,292,436, modified as described herein, to give the title compound in 82% yield (as determined by HPLC) in agueous solution. A reaction mixture prepared as in Step B was maintained at a temperature of about −50°. Diisopropylethylamine (1.06 g, 8.21 mmole) was added, followed by benzyl formimidate (1.09 g, 6.35 mmole). The mixture was stirred vigorously for 20 minutes at −50°, after which HPLC indicated residual unreacted aminoethylthio intermediate. Additional benzyl formimidate (0.05 g) was added and the mixture was warmed to −20° over a fifteen-minute period and held at −20° for 20 minutes. The reaction mixture was poured into a mixture of water (150 ml), butanol (120 ml), ethyl acetate (60 ml), and 0.5M N-methylmorpholine (60 ml) at 5° and pH 6.8. Hydrogenolysis of the mixture was performed in an unthermostatted autoclave at 15° (initial) to 23° (final) using hydrogen gas (100 psi) over 20% Pd(OH)$_2$ on carbon catalyst (0.9 g) for 1.5 hours. The mixture was filtered at 5° through a filter aid. The aqueous layer was separated and assayed for N-formamidoylthienamycin.

EXAMPLE 4

N-Formamidoylthienamycin, Method B

The title compound was prepared according to the method of Example 3 except that ca. 81% pure bis(2,4-dichlorophenyl)phosphorochloridate, prepared as described in Example 2, was used. That is, 3.04 g of the phosphorochloridate-phosphate mixture (containing ca. 2.46 g of the phosphorochloridate) was allowed to react with 1.80 g of p-nitrobenzyl (3R,5R,6S)-2-oxo-6-[(1R)-1-hydroxyethyl]carbapenem-3-carboxylate. Subsequent reaction with cysteamine hydrochloride, amidine formation, and hydrogenolysis of the ester group yielded the title compound in 82% yield (as determined by HPLC) in aqueous solution.

What is claimed is:

1. A process for preparing a phosphorohalidate having the formula:

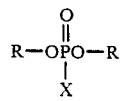

wherein
R is phenyl or phenyl substituted with 1 to 3 substituents selected from the group consisting of:
  (i) halogen;
  (ii) C$_1$–C$_6$ alkyl;
  (iii) C$_1$–C$_6$ alkoxy;
  (iv) C$_1$–C$_4$ fluorinated alkyl; or
  (v) NO$_2$; and
X is chlorine or bromine,
comprising reacting a phosphorus oxyhalide of the formula POX$_3$, wherein X is defined as above, with an approximately one-fold to two-fold quantity of a phenol of the formula R—OH, wherein R is defined as above, in the presence of a dialkylaminopyridine or a hydrohalide salt thereof at a temperature of from about 100° up to about the boiling point of the reaction mixture.

2. A process according to claim 1 wherein the dialkylaminopyridine is 4-dimethylaminopyridine.

3. A process according to claim 1 wherein X is chlorine.

4. A process according to claim 1 wherein R is 2,4-dichlorophenyl.

5. A process according to claim 1 wherein the temperature is about 120°.

6. A process according to claim 1 for preparing bis(2,4-dichlorophenyl)phosphorochloridate having the formula

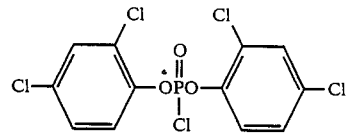

comprising reacting phosphorus oxychloride with an approximately 1.2-fold to 2.0-fold molar quantity of 2,4-dichlorophenol in the presence of 4-dimethylaminopyridine or 4-dimethylaminopyridine hydrochloride at a temperature of about 120°.

7. A process according to claim 1 wherein the phosphorohalidate is isolated by crystallization.

8. A process according to claim 7 comprising
  (a) reacting a phosphorus oxyhalide of the formula POX$_3$ with an approximately one-fold to two-fold molar quantity of a phenol of the formula R—OH in the presence of a dialkylaminopyridine or a hydrohalide salt thereof at a temperature of from about 100° up to about the boiling point of the reaction mixture;
  (b) adding a substantially inert crystallization solvent at a temperature below the boiling point of the crystallization solvent;
  (c) removing insoluble material from a resultant solution of the phosphorohalidate in the crystallization solvent;
  (d) cooling the solution to a temperature of from about 0° to about −40°; and
  (e) collecting the phosphorohalidate that crystallizes.

9. A process according to claim 8 wherein the crystallization solvent is an alkaline of from about 5 carbon atoms to about 9 carbon atoms.

10. A process for preparing bis(2,4-dichlorophenyl)-phosphorochloridate having the formula

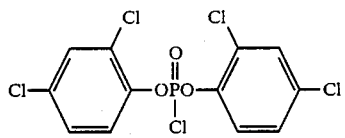

comprising
(a) reacting phosphorus oxychloride with an approximately 1.2-fold to 2.0-fold molar quantity of 2,4-dichlorophenol in the presence of 4-dimethylaminopyridine or 4-dimethylaminopyridine hydrochloride at a temperature of about 120°;
(b) adding hexane at a temperature below the boiling point of hexane;
(c) removing insoluble material from a resultant solution of the bis(2,4-dichlorophenyl)phosphorochloridate in hexane;
(d) cooling the solution to a temperature of from about 0° to about −40°; and
(e) collecting the bis(2,4-dichlorophenyl)phosphorochloridate by filtration.

11. A process comprising
(a) reacting a phosphorus oxyhalide of the formula $POX_3$ with an approximately one-fold to two-fold molar quantity of a phenol of the formula R—OH in the presence of a dialkylaminopyridine or a hydrohalide salt thereof at a temperature of from about 100° up to about the boiling point of the reaction mixture;
(b) adding hexane at a temperature below the boiling point of hexane;
(c) removing insoluble material from a resultant solution of the phosphorohalidate in the hexane;
(d) cooling the solution to a temperature of from about 0° to about −40°; and
(e) collecting the phosphorohalidate that crystallizes; wherein:
X is chlorine or bromine; and R is phenyl or phenyl substituted with 1 to 3 substituents selected from the group consisting of: (i) halogen, (ii) $C_1$–$C_6$ alkyl, (iii) $C_1$–$C_6$ alkoxy, (iv) $C_1$–$C_4$ fluorinated alkyl, and (v) $NO_2$.

* * * * *